United States Patent [19]

Frick, Jr. et al.

[11] 4,298,747
[45] Nov. 3, 1981

[54] BIS(DIHYDROXYMETHYLOX-OIMIDAZOLIDINYL)ALKANES

[75] Inventors: John G. Frick, Jr., New Orleans; Robert J. Harper, Jr., Metairie, both of La.

[73] Assignee: The United States of America as represented by the Secretary of Agriculture, Washington, D.C.

[21] Appl. No.: 180,544

[22] Filed: Aug. 25, 1980

[51] Int. Cl.$^3$ ............................................. C07D 233/40
[52] U.S. Cl. .......................................... 548/318; 8/186
[58] Field of Search ............................ 548/318; 8/186

[56] References Cited

U.S. PATENT DOCUMENTS

| | | | |
|---|---|---|---|
| 2,777,857 | 1/1957 | Konig | 548/318 |
| 3,112,156 | 11/1963 | Vail et al. | 8/116.3 |
| 3,260,565 | 7/1966 | Beachem | 8/116.3 |
| 3,814,580 | 6/1974 | Pruckmayr | 548/318 X |

OTHER PUBLICATIONS

Chemical Abstracts, 78:44433h (1973) [Niebergall, H., et al., *Angew. Makromol. Chem.* 1972, 27, 113–128].
Bullock, A., et al., *Analytical Chem.*, 42(14), 1783–1786 (1970).
Dinwoodie, A., et al., *J. Chem. Soc.* (C), 1967, 2565–2568.

*Primary Examiner*—Richard A. Schwartz
*Attorney, Agent, or Firm*—M. Howard Silverstein; David G. McConnell; Raymond C. Von Bodungen

[57] ABSTRACT

New compounds in the class of α,ω-bis(4,5-dihydroxy-3-methyl-2-oxoimidazolidin-1-yl)alkanes have been prepared from the reaction of glyoxal and an alkylenebis(3-methylurea). These compounds are useful as formaldehyde-free finishing agents for textiles containing cellulose.

3 Claims, No Drawings

BIS(DIHYDROXYMETHYLOXOIMIDAZOLIDI-NYL)ALKANES

BACKGROUND OF THE INVENTION (1) Field of the Invention

This invention relates to formaldehyde-free finishing agents for increasing wrinkle resistance in textiles.

(2) Description of the Prior Art

Textiles composed of cellulose, such as cotton or rayon and their mixtures with synthetic fibers, are often finished with chemical agents to impart the ability to resist wrinkling and musing in use and during laundering. These agents also reduce fabric shrinkage due to laundering. These finishing agents are compounds that contain two or more groups capable of reaction with cellulose. During the finishing operation, the agent reacts with two polymeric cellulose molecules to form crosslinks or bridges between the cellulose chains.

The finishing agents now in common use are prepared from the reaction of formaldehyde and amides to form methylol compounds, or hydroxymethylamides. Typical examples are 1,3-dimethylolurea, 1,3-dimethylol-2-imidazolidinone, and 4,5-dihydroxy-1,3-dimethylol-2-imidazolidinone. These agents are quite effective for the intended purpose. However, the agents and their reaction products on the finished fabric often decompose or hydrolyze slowly releasing formaldehyde. This is a decided drawback because even small amounts of formaldehyde are irritating and may be hazardous.

To avoid formaldehyde release, agents have been sought that are not made from formaldehyde and do not release formaldehyde on decomposition. Such agents have been made from the reaction of glyoxal and a urea to make 4,5-dihydroxy-2-imidazolidinone and its derivatives as described in U.S. Pat. Nos. 3,112,156 and 3,260,565. In reaction with cellulose, these compounds are difunctional, the minimum functionality required to produce crosslinks. As finishing agents, these compounds are not as effective as the compounds made from formaldehyde. They can not impart the degree of wrinkle resistance imparted by the compounds made from formaldehyde.

Compounds containing more than two reactive groups have been made from glyoxal and monoureas. An example is 1,2-bis(4,5-dihydroxy-2-oxoimidazolidin-1-yl)-1,2-dihydroxyethane prepared by A. H. Dinwoodie, G. Fort, and J. M. C. Thompson, Journal of the Chemical Society C1967, (23), 2565–2568. These compounds should be more reactive because of their greater functionality. However, these compounds also contain other hydroxyl groups that interfere in their reaction with cellulose. They are, therefore, relatively ineffective as finishing agents.

SUMMARY OF THE INVENTION

The object of this invention is to provide new compounds for use as formaldehyde-free finishing agents for cellulose-containing textiles. The compounds have the structure

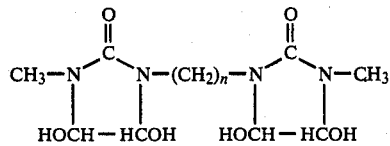

where n is 2 or 3.

DESCRIPTION OF THE PREFERRED EMBODIMENTS

The compounds of this invention are prepared by the reaction of the appropriate alkylenebis(3-methylurea) with two molar equivalents of glyoxal in water solution. The reaction can be conducted over a wide range of pH and temperature although usually we have used pH about 8 and room temperature (about 23° C.). A pH above 8.5 should be avoided to prevent side reactions of glyoxal. To isolate the compounds, the reaction mixture is concentrated under vacuum, and the compound is crystallized from the residual concentrate. The compound can be purified by recrystallization.

Although isolation gives a compound that is a more effective finishing agent, the reaction mixture without purification can be used also to finish textiles.

These compounds can be used as finishing agents in a manner similar to that used with the methylol amides made from formaldehyde. They are applied to textiles from water solution with a mildly acidic salt such as magnesium chloride, zinc nitrate, or ammonium chloride. The textile is then dried and heated briefly at 140°–160° C. to promote the reaction.

The following examples will illustrate the preparation and use of the new compounds.

EXAMPLE 1

1,2-Bis(4,5-dihydroxy-3-methyl-2-oxoimidazolidin-1-yl)ethane was prepared as follows:

A neutralized 40% solution of glyoxal, 11.5 g, was diluted with 16.4 g water, and the diluted solution mixed with 7.0 g ethylenebis(3-methylurea). The mixture was warmed to 60° C. to dissolve all reagents and adjusted to pH 8. It was allowed to cool and stand for four days. The solution was then evaporated under vacuum at room temperature to 15 g liquid residue that partially solidified on standing. The solid was filtered and washed with a little cold water to give 6.8 g of 1,2-bis(4,5-dihydroxy-3-methyl-2-oxoimidazolidin-1-yl)ethane, m.p. 158°–161° C. Recrystallization from a solvent of 60% methanol and 40% toluene by volume gave 4.3 g, m.p. 166°–168° C.

A water solution with 9.8% of the 1,2-bis(4,5-dihydroxy-3-methyl-2-oxoimidazolidin-1-yl)ethane and 2.0% magnesium chloride hexahydrate adjusted to pH 5 was applied to cotton printcloth. The amount of solution applied was about 90% of the fabric weight. The fabric was dried and then heated 3 minutes at 150° C. After treatment, the fabric could be washed and dried with less wrinkling and resisted wrinkling in use. In tests described by the American Association of Textile Chemists and Colorists, durable press rating was 3.3 and wrinkle recovery angle, as sum of test results in warp and fill directions, was 262°.

EXAMPLE 2

1,3-Bis(4,5-dihydroxy-3-methyl-2-oxoimidazolidin-1-yl)-propane was prepared as follows.

A 14.5 g portion of neutralized 40% glyoxal was diluted with 15.4 g water, and the diluted solution was mixed with 9.4 g trimethylenebis(3-methylurea). The mixture was warmed to 60° C. to dissolve all reagents and adjusted to pH 8. The solution was allowed to cool and stand 4 days. It was then evaporated under vacuum at room temperature to 17 g of liquid residue in which a solid formed on standing. The solid was filtered and washed with a little cold water to give 2.8 g of 1,3-bis(4,5-dihydroxy-3-methyl-2-oxoimidazolidin-1-yl)propane. After recrystallization from a mixture of 50% methanol and 50% toluene by volume, the compound melted at 141°–143° C.

We claim:

1. A bis substituted alkane compound having the following structure:

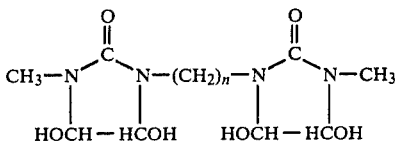

wherein n is 2 or 3.

2. The bis substituted alkane compound of claim 1 which is 1,2-bis(4,5-dihydroxy-3-methyl-2-oxoimidazolidin-1-yl)ethane.

3. The bis substituted alkane compound of claim 1 which is 1,3-bis(4,5-dihydroxy-3-methyl-2-oxoimidazolidin-1-yl)propane.

* * * * *